United States Patent
Wolf et al.

(10) Patent No.: US 7,118,758 B1
(45) Date of Patent: Oct. 10, 2006

(54) TRANSFORMED BACTERIA PRODUCING CS6 ANTIGENS AS VACCINES

(75) Inventors: Marcia K. Wolf, Silver Spring, MD (US); Fred J. Cassels, Ellicott City, MD (US); Edgar Charles Boedeker, Crownsville, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

(21) Appl. No.: 09/479,877

(22) Filed: Jan. 10, 2000

Related U.S. Application Data

(63) Continuation of application No. 08/788,145, filed on Jan. 24, 1997, now abandoned.

(51) Int. Cl.
*A61K 39/108* (2006.01)

(52) U.S. Cl. .................. 424/257.1; 424/185.1; 424/234.1; 424/241.1; 530/350

(58) Field of Classification Search .............. 435/252.1, 435/69.1; 424/200.1, 499, 261.1, 235.1, 243.1, 424/203.1, 241.1, 234.1, 185.1, 257.1; 530/350; 536/23.2
See application file for complete search history.

(56) References Cited

U.S. PATENT DOCUMENTS

| | | | | |
|---|---|---|---|---|
| 4,761,372 A | * | 8/1988 | Maas et al. | 435/172.1 |
| 5,017,372 A | * | 5/1991 | Hastings | 424/85.8 |
| 5,417,986 A | * | 5/1995 | Reid et al. | 424/499 |
| 5,698,416 A | * | 12/1997 | Wolf et al. | 435/69.1 |
| 5,874,088 A | * | 2/1999 | Mekalanos | 424/200.1 |
| 5,935,838 A | * | 8/1999 | Askelof et al. | 435/252.1 |

OTHER PUBLICATIONS

Rudin, A et al, Microbial pathogenesis, Feb. 1994, vol. 16(2), pp. 131–139.*
Reeck, Gerald R et al, Cell, vol. 50, p. 667, Aug. 28, 1987.*
Lewin, Roger, Science, Vo.. 237, p. 1570, 1987.*
Ellis, Ronald W., Chapter 29, New Technologies for Making Vaccines, Vaccines, pp. 568–575, WB Saunders Company, Plotkin and Mortimer.*
Grewel, HM et al, VAccine, vo.. 11(2), pp. 221–226, 1993.*
Thomas, LV et al, J. Gen. Microbiol., vol. 131(pt. 9), pp. 2319–2326, Sep. 1985.*
Wolf, MK et al, Infection and Immunity, vol. 57(1), pp. 164–173, Jan. 1989.*
Ahren, CM et al, Oct. 1985, vol. 50(1), pp. 255–261, Infection and Immunity.*
Willshaw, GA et al, FEMS Microbiol. Lett. vol. 49, p. 473–478, 1988, sequence alignment, Accession No. I83348, abstract only.*
Knutton, S et al, Infection and Immunity, vol. 55(1), pp. 86–92, Jan. 1987.*
McConnell, MM et al, Infection and Immunity, Aug. 1988, vol. 56(8), pp. 1974–1980.*
Grewal, HM et al, J. Clin. Microbiol. vol. 32, pp. 1295–1301, 1994.*

* cited by examiner

*Primary Examiner*—Mark Navarro
*Assistant Examiner*—Ginny Allen Portner
(74) *Attorney, Agent, or Firm*—Elizabeth Arwine; Charles H. Harris

(57) ABSTRACT

Disclosed herein are antigens that stimulate protective antibodies against enterotoxigenic *Escherichia coli*. Also disclosed herein are proteins encoded by cssA and cssB genes as well as constructs containing the genes and methods of using thereof.

2 Claims, 1 Drawing Sheet

TRANSFORMED BACTERIA PRODUCING CS6 ANTIGENS AS VACCINES

This application is a continuation of patent application U.S. Ser. No. 08/788,145 filed Jan. 24, 1997 now abandoned, which is a continuation-in-part of patent application U.S. Ser. No. 08/243,482 filed May 13, 1994, which is now abandoned.

FIELD OF THE INVENTION

This invention is related to a CS6 antigen for use in vaccines to protect from pathological effects of enterotoxigenic E. coli.

BACKGROUND OF THE INVENTIONS

CS6 is a component of CFA/IV (colonization factor antigen IV), one of three CFAs commonly found on enterotoxigenic Escherichia coli (ETEC). A recent study showed CS6 on 31% of ETEC isolated from soldiers in the Middle East. Other CFAs and similar proteins found on the surface of ETEC function as adhesins to attach bacteria to intestinal epithelial cells. Attached bacteria can then deliver their toxin(s) to the target cells. It has never been proved that CS6 is an adhesin for human tissue (Knutton, S., M. M. McConnell, B. Rowe, and A. S. McNeish, "Adhesion and Ultrastructural Properties of Human Enterotoxigenic Escherichia coli Producing Colonization Factor Antigens III and IV", Infect.Immun. 57:3364–3371 (1989)), but a study in rabbits indicated CS6 is a colonization factor.

The CS6 operon has much in common with fimbrial operons from E. coli, Salmonella, Yersinia, Klebsiella, Haemophilus, and Bordetella. All contain molecular chaperons and ushers and a number of structural subunits. This area contains two sequences homologous to insertion sequences, but no complete insertion sequences.

The low GC content (34%) and codon usage that is characteristic of E. coli genes that are expressed at low levels suggest the CS6 genes may have originated in another species. GC content of 35–45% is characteristic of Gram positive bacteria such as Staphylococcus, Streptococcus, Bacillus, and Lactobacillus. Low GC content is common for virulence-associated genes of E. coli.

CS6 is unusual because it is expressed on bacteria grown on a variety of media, unlike other CFA's from ETEC that are only expressed on bacteria grown on CFA agar. This unusual regulation is not peculiar to strain E8775 because ETEC isolated in 1990 expressed CS6 when grown on L agar. Temperature regulation of CS6 expression is characteristic of other CFA's from ETEC and virulence genes in a variety of pathogenic bacteria.

Although CS6 has never been visualized by negative staining, electron microscopy using anti-CS6 sera and colloidal gold indicated that it is present on the surface of ETEC. The apparent major protein associated with CS6 is approximately 16 kDa which is in the range of molecular weights typical for subunits for fimbriae and fibrillae. CS6 from ETEC strain E10703 of serotype 0167:H5 has been cloned (Willshaw, et al., FEMS Microbio. Let. 49: 473–478 (1988)). Only 3 kb of DNA was necessary for expression of CS6. That is in contrast to fimbriae that typically require approximately 9 kb of DNA and include genes for subunits as well as proteins for transport of subunits and synthesis and assembly on the bacterial surface.

Grewal teaches bacterial strains transformed with plasmids containing genes which encode CS6. However, that reference does not teach use of plasmids under the controls of a lac promotor and a CS6 promotor.

DESCRIPTION OF THE INVENTION

Figure 1:
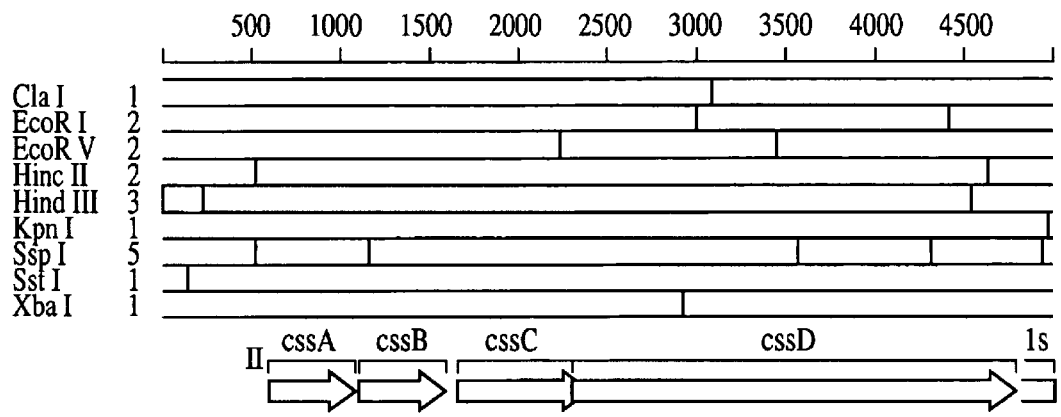
FIG. 1 shows the restriction sites and the location of the pertinent genes that make up the CS6 operon.
Figure 2:
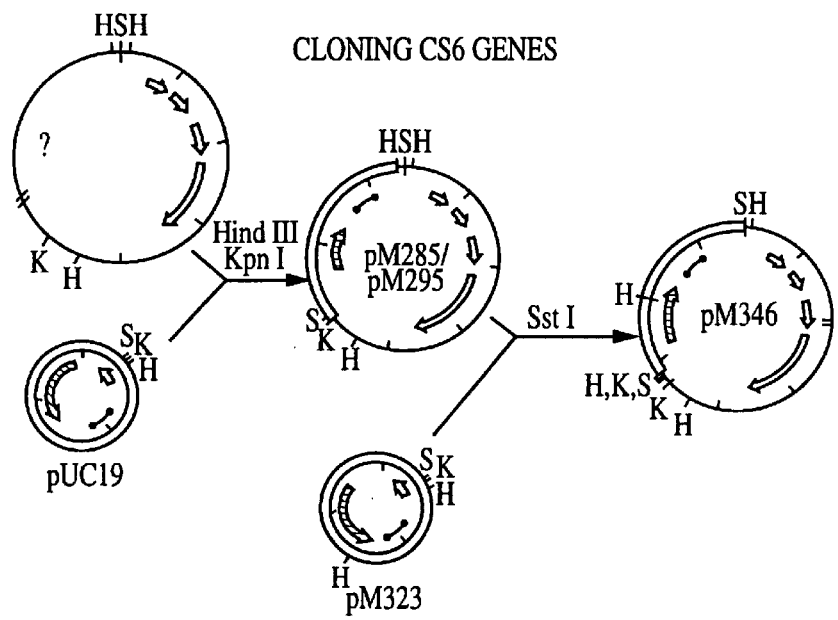
FIG. 2 shows derivation of the clone containing the kanamycin resistance gene.

It is the purpose of this invention to provide structural proteins which will act as antigens to stimulate protective antibodies against enterotoxigenic Escherichia coli. Particularly important are proteins having the antigenic properties of the proteins encoded by the cssA and cssB genes. Constructs may be prepared which encode either one or both of the proteins. However, both proteins would be needed to provide desirable protection. The CS6 operon includes four genes which we designate cssA, cssB, cssC, and cssD. cssA and CssB encode the structural proteins of CS6. The CS6 operon has much in common with fimbrial operons from E. coli, Salmonella, Yersinia, Klebsiella, Haemophilus, and Bordetella. All contain molecular chaperons and ushers and a number of structural subunits. In a preferred embodiment, plasmids containing all four genes are transformed into attenuated bacteria, which are then given by mouth to prevent morbidity arising from infection with E. coli.

CS6 has two major subunits; protein sequencing data demonstrates that CS6A and CS6B are both present. The DNA sequence yields a mechanism for expression of similar amounts of the two proteins. The CS6 operon contains DNA immediately downstream of cssB which can form a stem-loop with a stem,rich in G and C which commonly act as transcription terminators. Termination at this site yields a transcript with cssA and cssB such that CssA and CssB proteins would be translated in equal amounts. Fimbrial operons for Pap, K99, and K88 have stem loops immediately downstream of the genes for the major coding structural subunits. This has been offered as a mechanism for over expression of subunit genes relative to other genes in the operons. In the case of CS6, this would allow over expression of both CS6A and CS6B.

The occurrence of two major structural proteins is unusual because fimbriae have a single major subunit and a number of minor subunits. CS3, which has been designated fibrillar rather than fimbrial, is an exception to this generality because it has 2 subunits. CssD belongs to the family of molecular ushers located in the outer membrane that accept subunits from the chaperone and escorts them to the bacterial surface. Apparently the entire cssD gene is not necessary for CS6 expression since CS6 was detected from clones carrying pDEP5 which only contains the N-terminal one-third of cssD. Klemm and Christiansen found that mutations in the usher for Type 1 fimbriae reduced fimbriation but 10% of the bacteria produced a few fimbriae (Mol.Gen.Genet. 220:334–338).

The CS6 proteins are produced in the transformed bacteria and are present on the exterior surface of the bacteria. These proteins give rise to immunological response in the host. For immunization, the bacteria may be given either dead or alive. When attenuated bacteria have been transformed, the bacteria can be given live in mildly basic carriers. Economical and readily available carriers include carbonated water which may be flavored. The administration of the transformed bacteria in carbonated beverages is particularly useful, since the means necessary for administration is widely available.

In a preferred embodiment, the products are produced under the control of a lac promotor from pUC19. In the preferred embodiment, a vector pM346 containing a kanamycin resistant gene makes it possible to provide products which are appropriate for use in humans.

The CS6 proteins may also be extracted from the supernatant of the culture containing the organisms which express the proteins. The proteins may then be administered orally. The proteins may be formulated by means known in the art, including microencapsulation, coated capsules and liposomes. The proteins may be lyophilized before formulation.

Materials and Methods
Source of Nucleic Acid

The genes for CS6 expression were from enterotoxigenic *Escherichia coli* (ETEC) strain E8775 tox⁻ of serotype 025:H42 which was a gift from Alejandro Cravioto. E8775 tox⁻ is a derivative of *E. coli* strain E8775 which was originally isolated from Bangladesh. DH5α which was purchased from Bethesda Research Laboratories, Inc., Gaithersburgs, Md. pUC19 was originally purchased from P-L Biochem.

The antibiotic resistance gene encodes resistance to kanamycin and was purchased from Pharmacia, Uppsala, Sweden ($Kan_R$ GenBlock®).

CS6 expression is regulated from its native promoter. That is demonstrated by retention of control by growth temperature and is consistent with the DNA sequence determined from the clone. A contribution of the lac promoter from pUC19 is undefined. The contribution of increased copy number of the plasmid is probably substantial.

The nucleotide sequence containing the coding region was determined to be as constructed containing the kanamycin resistance gene was as follows:

```
   1 AAGCTTGTAA CCAGTTGATA AAAATATATC ACGCTGGGAA TGACGTGATG  Sequence ID No. 1

51 TATATACGGA GCAGCTATGT CGGAACAGAT ATTTTCCTAT CGGTATGCGT

101 TGTGAGTAAG CGTAAAGCCA ATGCTGTCTG TAACTCCTGA TCCTTGCAGA

151 CTAAATTAGA GCTCCTTCTA AATTAGACGG ATGGATAAAC CTACAGACTG

201 GCGCTCTGGG TCTCGCCGGA TATTTTCTAA TGAATTTAAG CTTCATATGG

251 TTGAACTGGC TTCGAAACCA AATGCCAATG TCGCACAACT GGCTCGGGAA

301 CATGGCGTTG ATAACAACCT GATTTTTAAA TAGCTACGCC TCTGGCAAAG

351 AGAAGGACGT ATTTCTCGTA GAATGCCTCC AACTATTGTA GGCCCTACAG

401 TACCACTGAG GTAGCCTGAA TTTAAAGCCG AAGCGGTCAG AACTGTTCTT

451 GGTGTGAACG TAGCACTCAC CAATAAAAGC ATCAATACGG TGCTCTGTTG

501 ACACATTACG AATGTTATGT ATACAATAAA AATGATTATA GCAATATTAA

551 TGGTGTTATA TGAAGAAAAC AATTGGTTTA ATTCTAATTC TTGCTTCATT

601 CGGCAGCCAT GCCAGAACAG AAATAGCGAC TAAAAACTTC CCAGTATCAA

651 CGACTATTTC AAAAAGTTTT TTTGCACCTG AACCACGAAT ACAGCCTTCT

701 TTTGGTGAAA ATGTTGGAAA GGAAGGAGCT TTATTATTTA GTGTGAACTT

751 AACTGTTCCT GAAAATGTAT CCCAGGTAAC GGTCTACCCT GTTTATGATG

801 AAGATTATGG GTTAGGACGA CTAGTAAATA CCGCTGATGC TTCCCAATCA

851 ATAATCTACC AGATTGTTGA TGAGAAAGGG AAAAAAAATGT TAAAAGATCA

901 TGGTGCAGAG GTTACACCTA ATCAACAAAT AACTTTTAAA GCGCTGAATT

951 ATACTAGCGG GGAAAAAAAA ATATCTCCTG GAATATATAA CGATCAGGTT

1001 ATGGTTGGTT ACTATGTAAA CTAAATACTG GAAGTATGAT TATGTTGAAA

1051 AAAATTATTT CGGCTATTGC ATTAATTGCA GGAACTTCCG GAGTGGTAAA

1101 TGCAGGAAAC TGGCAATATA AATCTCTGGA TGTAAATGTA AATATTGAGC

1151 AAAATTTTAT TCCAGATATT GATTCCGCTG TTCGTATAAT ACCTGTTAAT

1201 TACGATTCGG ACCCGAAACT GGATTCACAG TTATATACGG TTGAGATGAC

1251 GATCCCTGCA GGTGTAAGCG CAGTTAAAAT CGCACCAACA GATAGTCTGA

1301 CATCTTCTGG ACAGCAGATC GGAAAGCTGG TTAATGTAAA CAATCCAGAT

1351 CAAAATATGA ATTATTATAT CAGAAAGGAT TCTGGCGCTG GTAACTTTAT

1401 GGCAGGACAA AAAGGATCCT TTCCTGTCAA AGAGAATACG TCATACACAT
```

-continued

```
1451 TCTCAGCAAT TTATACTGGT GGCGAATACC CTAATAGCGG ATATTCGTCT

1501 GGTACTTATG CAGGAAATTT GACTGTATCA TTTTACAGCA ATTAAAAAAA

1551 GGCCGCATTA TTGCGGCCAT TGACGATACT GCTAGGCAAA AATATGAAAT

1601 CAAAGTTAAT TATACTATTG ACGTTAGTGC CATTTTCATC TTTTTCAACA

1651 GGAAATAATT TTGAAATAAA TAAGACACGA GTAATTTACT CTGACAGCAC

1701 ACCATCAGTT CAAATATCAA ATAATAAAGC ATATCCTTTA ATTATTCAAA

1751 GCAATGTATG GGATGAAAGC AATAATAAAA ATCATGACTT TATAGCAACA

1801 CCACCGATTT TTAAAATGGA AAGTGAAAGT CGGAATATAA TAAAAATAAT

1851 TAAAACAACT ATTAATTTGC CGGACTCTCA GGAAAGTATG AGATGGTTAT

1901 GTATTGAATC AATGCCACCA ATAGAAAAAA GTACTAAAAT AAACAGAAAA

1951 GAAGGAAGGA CAGACAGTAT TAATATCAGC ATTCGGGGGT GCATTAAACT

2001 GATATATCGA CCTGCCAGTG TTCCGTCTCC TGTTTTTAAT AATATAGTAG

2051 AAAAATTAAA ATGGCATAAA AATGGAAAGT ATCTTGTATT AAAAAATAAT

2101 ACACCCTATT ACATTAGCTT TTCTGAGGTT TTTTTTGATT CAGATAAAGT

2151 AAACAATGCA AAAGATATTT TATATGTAAA ACCATACTCA GAGAAGAAAA

2201 TAGATATCAG CAACAGAATA ATAAAAAAAA TCAAATGGGC TATGATTGAT

2251 GATGCTGGCG CAAAAACAAA ACTTTATGAA TCAATTTTAT AAAAAATCTC

2301 ATTACAGTAT ACAAAAACAT CAGATTACAG GCTTGCTTTT TTTGCTATTT

2351 ATATATCCTT TCTCAACCTC ATATGGAAAT GAACAATTTA GTTTTGACTC

2401 ACGATTCCTA CCATCAGGTT ATAATTACTC TTTAAATAGT AACTTACCTC

2451 CTGAAGGTGA GTATCTGGTT GATATTTATA TTAACAAAAT AAAAAAGGAG

2501 TCCGCGATTA TTCCTTTTTA TATAAAAGGA AATAAACTTG TACCATGTTT

2551 ATCAAAAGAA AAAATTTCAT CTTTGGGTAT CAACATTAAT AATAACGACA

2601 ACACAGAGTG TGTAGAAACA AGTAAGGCAG GTATTAGTAA TATCAGCTTT

2651 GAGTTTAGCT CTCTTCGTTT GTTTATTGCT GTACCGAAAA ATCTTCTGTC

2701 TGAGATTGAT AAAATATCAT CAAAGGATAT AGATAACGGG ATTCATGCTT

2751 TATTTTTTAA TTATCAAGTA AATACAAGGC TAGCCAATAA TAAAAATCGT

2801 TATGATTACA TTTCTGTTTC ACCAAATATA AATTATTTTT CATGGCGGTT

2851 GCGTAATCTT TTTGAATTTA ACCAAAACAA CGATGAAAAA ACATGGGAAA

2901 GAAACTACAC TTATCTAGAA AAAAGTTTTT ATGATAAAAA GCTAAACTTA

2951 GTCGTTGGTG AAAGTTATAC GAATTCAAAT GTTTATAATA ACTACTCTTT

3001 TACTGGTATT TCAGTTTCTA CAGATACAGA TATGTATACG CCAAGTGAAA

3051 TCGATTATAC ACCAGAAATT CATGGAGTGG CTGATTCAGA CTCTCAGATT

3101 ATTGTCAGGC AAGGCAACAC CATTATCATT AATGAAAGTG TTCCAGCCGG

3151 ACCGTTCTCA TTTCCAATAA CCAATCTCAT GTATACTGGG GGGCAACTTA

3201 ATGTGGAGAT AACAGATATT TATGGAAATA AAAAACAATA TACTGTCAAT

3251 AATTCCTCTC TTCCTGTTAT GAGAAAAGCG GGACTAATGG TATATAATTT

3301 TATATCTGGG AAATTAACAA AAAAAAATAG TGAGGATGGT GATTTTTTTA

3351 CTCAAGGTGA TATTAACTAC GGTACTCACT ATAACAGCAC ACTATTCGGT

3401 GGATATCAGT TTAGTAAAAA TTATTTTAAC TTATCTACTG GTATAGGCAC
```

```
-continued
3451 TGATCTGGGA TTTTCTGGAG CATGGCTACT ACACGTTAGC AGAAGTAATT

3501 TTAAGAATAA AAATGGATAT AATATTAATC TACAACAAAA CACTCAGTTA

3551 AGACCATTCA ATGCCGGGGT TAATTTCGAT TACGCATACA GAAAAAAAAG

3601 GTATGTGGAA CTTTCCGACA TTGGCTGGCA TGGTAATTTA TATAATCAAC

3651 TTAAAAATAG TTTTTCTTTA TCCTTGTCAA AATCATTGAA TAAATACGGA

3701 AATTTCTCAC TTGATTATAA CAAAATGAAA TACTGGGATA ATGCGTATGA

3751 TAGTAACTCA ATGTCGATTC GTTATTTTTT TAAATTCATG CGAGCAATGA

3801 TTACAACAAA TTGTTCTTTA AATAAATATC AATCTTATGA AAAAAAAGAT

3851 AAAAGATTTA GTATTAATAT ATCATTGCCT TTAACCAAAG ATTACGGGCA

3901 CATATCTTCA AACTATTCAT TTTCCAATGC AAATACAGGA ACGGCAACCA

3951 GTTCTGTAGG CTTAAACGGT AGTTTTTTTA ATGACGCAAG ATTAAACTGG

4001 AACATTCAGC AGAACAGAAC GACCCGTAAC AATGGATATA CTGATAATAC

4051 CAGTTACATA GCAACCAGCT ATGCCTCTCC CTATGGCGTT TTTACTGGTT

4101 CATATTCAGG ATCGAACAAG TATTCAAGCC AGTTTTATTC TGCATCGGGA

4151 GGTATTGTTT TGCATAGCGA TGGCGTAGCT TTTACTCAAA AAGCCGGAGA

4201 TACCTCTGCT CTTGTCCGTA TTGATAATAT TTCTGATATA AAAATTGGTA

4251 ACACTCCTGG TGTTTATACT GGGTATAATG GTTTTGCTTT AATTCCTCAT

4301 CTTCAGCCGT TCAAAAAAAA CACCATTTTA ATTAATGATA AAGGAATTCC

4351 AGACGGTATT ACTCTTGCTA ATATAAAAAA ACAAGTTATC CCATCACGAG

4401 GAGCTATTGT TAAAGTAAAA TTTGATGCTA AAAAAGGCAA TGACATTTTG

4451 TTTAAGCTTA CAACTAAAGA TGGAAAAACG CCCCCATTAG GAGCTATAGC

4501 CCATGAAAAA AATGGAAAAC AGATTAATAC GGGTATCGTT GACGATGATG

4551 GTATGCTTTA TATGTCTGGA TTATCAGGGA CAGGGATTAT TAATGTAACA

4601 TGGAATGGAA AAGTCTGTTC ATTTCCTTTT TCAGAAAAAG ATATATCTAG

4651 CAAACAATTA TCTGTTGTAA ATAAACAATG TTAGGTAGTG CATCCAATTA

4701 GTAGAACATG TGTTTTTCGA TAAACGCTCC GATCTCTTTT TCGTGGATCT

4751 CAACTGAGCG TGAGAAGCAG ATTGTTTTAC GAGCCAACCG CTTAATGCGG

4801 GTGCGTAGCG TCAGATTATT ACGCTCAATG CGTTGGGTGA ATATTTTGCC

4851 GGTCAGATGC TTATTCTTCG GTACC
```

Cell Expression Clone:

E. coli HB101 was purchased from the American Type Culture Collection, Rockville, Md. It is ATCC #33694 and batch #91-1. (Eerichia coli ATCC 33694) Preceptrol [Reg TM] culture. D. Ish-Horowicz and J. F. Burke HB101 ← H. Boyer. Genotype: F- leuB6 proA2 recA13 thi-1 ara-14 lacY1galK2 xyl-5 mtl-1 rpsL20 supE44 hsdS20 (r- B m- B at least thi-hsd from Escherichia coli B). Produces isoprene (Curr. Microbiol. 30:97–103, 1995). J. Mol. Biol. 41: 459–472, 1969; Methods Enzymol. 68: 245–267, 1979.) Growth Conditions: Medium 1065 37C.

The plasmid containing the CS6 genes, the pUC19 origin of replication, and the gene for kanamycin resistance was transferred into E. coli HB101 by transformation. Transformants were selected by growth on L agar supplemented with 0.04% Xgal with 50 μgm per ml kanamycin sulfate and/or 50 μgm per ml ampicillin.

One copy of the CS6 genes exists as an extrachromosomal plasmid of high (500–700) copy number. The CS6 genes are present on a plasmid, not integrated into the chromosome. The plasmid has been isolated from the strain and examined by agarose gel electro-phoresis.

Plasmid DNA from E8775 tox⁻ was transferred to laboratory strain DH5α as a cointegrate with F' $lac_{ts}$::Tn5, a conjugative plasmid. Transfer of the F' $lac_{ts}$::Tn5 plasmid was selected by antibiotic resistance to kanamycin and CS6 expression was detected by Western blot using polyclonal antisera specific for CS6. Plasmids were isolated and a cointegrate was identified based on the large size. A spontaneous derivative in which the F' $lac_{ts}$::Tn5 was removed was obtained and named M56. M56 contains a 61-megadalton plasmid from E8775 tox⁻ and expresses CS6. Plasmid DNA from M56 was isolated, partially digested with restriction enzyme HindIII, and ligated to pUCl9 that had been digested with HindIII. The ligation mixture was transformed into DH5α and plated onto L agar supplemented with ampicillin and X-gal. White (lac⁻) colonies were picked to CFA plates supplemented with ampicillin and tested for CS6 expression.

A stable clone named M233 with an insert of approximately 24 kb into the cloning site of pUC19 was obtained. It was a spontaneous deletion of a larger clone. Subclones were obtained by digestion with various enzymes and a subclone containing approximately 5kb from the HindIII site to KpnI site was found that expressed. CS6. This clone was designated M285. Expression of CS6 was verified by transferring plasmids into E. coli strain HB101 and detecting CS6 expression. The cloned CS6 is expressed under the same conditions as CS6 from the native 61-megadalton plasmid: CS6 was detected in extracts from bacteria grown at 37° C. on CFA agar, L agar or MacConkey agar. CS6 was not expressed on bacteria grown at 17° C.

Studies were performed to determine appropriate handling of strain M285 for reproducible expression of CS6. Growth temperature was found to be especially important.

As indicated above, the protein sequence of the N-terminus of CS6 was determined from strains E8775 and from M233, the large clone derived from E8775. The 16 kDa proteins recovered from heat, saline extracts, and ammonium sulfate precipitation of M233 yielded two amino acids at each position (except cycle 12) indicating that two proteins were present. From the strength of the two signals, a probable primary sequence and a probable secondary sequence call was made for each of fifteen cycles. Quantitative analysis of the peak areas indicated that the molar ratio of the primary sequence (CS6A) to secondary sequence (CS6B) was approximately 3:1. The presence of the same two proteins was evident from strain E8775 grown on CFA agar and on L agar.

The DNA sequence of the DNA inserted into pUC19 in clone M285 was determined. Wim Gaastra's group in the Netherlands independently determined the DNA sequence of CS6 genes from ETEC strain E10703. The DNA sequences are available from Genebank accession numbers U04846 and U04844, respectively. A stretch of DNA of 4,219 base pairs was 98% identical. The DNA sequences diverge abruptly on both sides of the common region, defining the limits of the CS6 genes. Four open reading frames were detected within the common area. These were designated cssA, cssb, cssC, and cssD.

The four open reading frames are preceded by consensus sequences for binding RNA polymerase and ribosomes. The first open reading frame, cssA was identified as the gene for the CS6 structural protein designated as the primary protein based on the amino acid N-terminal sequence. The deduced molecular weight agrees with that previously determined from SDS PAGE. cssA includes a signal sequence that is typical for many exported proteins,. Eleven of 136 residues differ between the deduced CssA proteins from E8775 and from E10704.

cssB begins 17 bases downstream from cssA. There is a typical signal sequence. cssB was identified as the gene for the CS6 structural protein designated as the sec ondary protein based on the amino acid N-terminal sequence. Five of 146 residues differ between the deduced CssA proteins from E8775 and from E10704.

A region of dyad symmetry is present 6 bases downstream from CssB in both clones. The sequence is GGCCGCATTATTGCGGCC(Sequence #2) in E8775 ETEC and GGCCGCATTATTGATTGCGGCC(Sequence #3)in E10703. Underlined bases form the G-C rich stem. The calculated free energy value of these structures is −14.8 kcal. Such structures are often found in fimbrial operons after the genes encoding structural proteins.

cssC begins 48 bases downstream from cssB. It has a typical signal sequence. The deduced proteins from both clones have 212 residues with 7 differences. A search of protein databases indicated CssC is homologous to chaperone proteins necessary for expression of a number of fimbriae. The structure of PapD, the chaperone protein for Pap fimbriae, has been solved by X-ray crystallography and regions important for conserving the structural domains have been identified. CssC conforms to this consensus.

The cssD gene begins 14 bases upstream of the end of cssC. The protein from E8775 is truncated relative to the protein from E10703 and there are 28 differences between CssD from E8775 and E10703. The deduced protein from cssD is homologous to molecular ushers. Overall, CssD and the other proteins are only around 30% identical and around 50% similar, but the nine proteins have areas of high homology dispersed throughout, especially the first 410 residues, and 4 cysteines (residues 91, 112, and two near the C-terminus) which are conserved in all ushers.

A region of dyad symmetry is present 347 base pairs into the CssD gene in both clones. The calculated free energy value of these structures is −7.2 kcal.

The plasmid from strain M285 was transformed into E. coli HB101 purchased from ATCC. The resulting strain was named M295. Expression of CS6 from M295 was achieved from small-scale fermentation. For production for human use, it was desirable to add a gene for resistance to kanamycin as the selectable marker. To that end, a vector was constructed based on pUC19 but with a gene for kanamycin resistance in place of the gene for ampicillin resistance. The CS6 genes from the pUC19 clone were subcloned into the new vector and transformed into E. coli HB101.

Vector pM323 was constructed as follows. The kanamycin resistance gene was purchased from Pharmacia, Uppsala, Sweden (Kan$_R$ GenBlock®) and inserted into a cloning vector by Dr. David Lanar at WRAIR. DNA including the gene was amplified by PCR using the plasmid from Dr. Lanar as template and primers flanking the multiple cloning site. A product of the desired size (1,580 bp) was obtained, but with much template present. To increase the purity of the 1,580 fragment, a second PCR reaction was performed, this time with a small amount of the first PCR reaction as template. This product was confirmed by agarose gel electrophoresis, then digested with restriction enzyme HincII to remove unwanted restriction enzyme recognition sites. This product was ligated to pUC19 digested with SspI. The ligation mix was transformed into E. coli DH5α and plated on L agar plates supplemented with kanamycin and Xgal. Isolate M318 had the desired phenotype of resistance to kanamycin and ampicillin with lacZ' intact. The gene for ampicillin resistance was removed to make a smaller vector. This was achieved by designing and synthesizing 2 oligonucleotides to amplify just the portion of pM318 with the gene for kanamycin resistance, the lacZ' gene carrying the multiple cloning site, and the origin of replication. PCR was performed, the product ligated then transformed into E. coli DH5α with selection on L agar plates supplemented with kanamycin and Xgal. Isolate M323 had the desired phenotype of resistance to kanamycin, sensitivity to ampicillin, and intact lacZ'. Restriction digest patterns confirmed the plasmid was a derivative of pUC19 with the gene for kanamycin resistance in place of the gene for ampicillin resistance.

The CS6 genes were cloned into vector pM323 from pM285. pM323 and pM285 were digested with restriction enzyme SstI, ligated, and transformed into E. coli DH5α with selection on L agar plates supplemented with kanamycin and Xgal. Isolate M334 was determined to express CS6. Plasmid analysis revealed M334 carried the CS6 genes and 2 copies of the vector. An attempt was made to remove one copy of vector and at the same time move the clone into HB101, the desired host strain for fermentation. Isolate M340 was determined to express CS6 and retained 2 copies of the vector. An isolated colony of M340 was shown to produce high amounts of CS6 and was saved as M346.

In another embodiment lacking the kanamycin resistance gene, clones from an ETEC strain of serotype O25:H42 were derived from E. coli E8775 which was originally isolated from samples from Bangladesh. E. coli M56, which contains a 61-megadalton plasmid from E8775 Tox⁻ and expresses CS6 has been described. The host for cloning was E. coli DH5α which was purchased from Bethesda Research Laboratories, Inc., Gaithersburg, Md. The host for plasmids used for production of heat, saline extracts was HB101 (EMBO J. 4:3887–3893 (1985)).

Clones from E8775 were routinely grown in L broth. Antibiotics were added to L broth supplemented with agar as follows. Ampicillin was added, when appropriate, at 50 µg/ml. Chloramphenicol was used at 30 µg/ml. X-Gal (5-bromo-4-chloro-3-indolyl β-D-galactopyranoside, Sigma) was added at 0.004%. CFA plates were prepared as previously described (*Infect.Immun*. 57:164–173 (1989)).

Cloning CS6 from E8775. The 61-megadalton plasmid from E. coli M56 was partially digested with HindIII and ligated to pUC19 that had been digested with HindIII. The ligation mixture was transformed into E. coli DH5α and plated onto L agar plates supplemented with ampicillin and X-gal. White (lac⁻) colonies were picked to CFA plates supplemented with ampicillin and tested for CS6 expression using antisera as described below. Plasmids were purified as described (*Infect.Immun*. 57:164–173 (1989)). Restriction enzymes were used according to the manufacturer's directions.

Detection of CS6 Expression. CS6 expression by bacterial colonies was detected after transfer to nitrocellulose and treatment as described by Mierendorf (*Methods Enzymol*. 152:458–469 (1987)). Primary antisera was specific for CS6 and was raised in rabbits and absorbed as previously described (*Infect.Immun*. 57:164–173 (1989)), except that rabbits were inoculated intravenously with live bacteria suspended in normal saline. Secondary antibody was peroxidase-conjugated goat anti-rabbit IgG (Cappel Laboratories, Cochranville Pa.) and detection was by TMB Substrate (Kirkegaard & Perry Laboratories, Inc., Gaithersburg Md).

Positive identification of CS6 was by western blots of heat, saline extracts. Heat, saline extracts were prepared from bacteria grown on the indicated media as described (*Infect.Immun*. 27:657–666 (1980)). Proteins were separated on precast 16% Tricine sodium dodecyl sulfate-polyacrylamide gels (SDS-PAGE, Novex Novel Experimental Technology, San Diego Calif.) and transferred to nitrocellulose. Blots were handled as described above for colony blots.

Determination of N-terminal sequence. Heat, saline extracts were obtained from E8775 or clones of E8775 grown on L agar or CFA. Partial purification of CS6 was obtained by ammonium sulfate precipitation, with extracts sequentially precipitated at 20%, 40%, then 60% saturation. Samples at 40% and 60% saturation were dialyzed against deionized water and loaded onto precast 16% Tricine SDS-PAGE (Novex, San Diego, Calif.). Proteins were blotted onto polyvinylidene difluoride (PVDF) membranes (Westrans, Schleicher & Schuell, Keene, N.H.), stained by Coomassie blue (Rapid Coomassie Stain, Diversified Biotech, Newton, Mass.) and bands of approximately 16 kDa were excised for automated gas-phase N-terminal sequencing analysis (Applied Biosystems Model 470A, Foster City, Calif.). Data were analyzed using the Model 610A Data Analysis Program, Version 1.2.1 (Applied Biosystems, Inc, Foster City, Calif.). These methods have been described in detail (*Infect.Immun*. 60:2174–2181 (1992)).

DNA sequencing. DNA sequencing of the clones derived from E8775 was performed using the Model 373A DNA sequencing system from Applied Biosystems, Inc, Foster City, Calif. Reactions were performed using the dideoxy method with fluorescent dye-labeled terminators, double-stranded templates, oligonucleotide primers, and AmpliTaq DNA polymerase following the manufacturer's protocol. Appropriate oligonucleotide primers were synthesized using a Model 391 DNA Synthesizer (Applied Biosystems, Inc, Foster City, Calif.). Plasmids were purified for use as templates by a slight modification of the alkaline lysis method and cesium chloride density gradient centrifugation described by Maniatis (*Molecular Cloning: A Laboratory Manual*, Cold Spring Harbor Laboratory, Cold Spring Harbor (1982)). Plasmids were recovered by dialysis followed by multiple ethanol precipitations to remove residual salt. Sequence analysis was performed using software developed by the University of Wisconsin Genetics Computer Group (*Nucleic Acids Res*. 12:387–395 (1984)).

Results

CS6 genes cloned from ETEC strain E8775 into pUC19. A stable clone named M233 was obtained from a partial digest of the 61-megadalton plasmid from E. coli M56. It was a spontaneous deletion of a larger clone. The insert in M233 was approximately 24 kb. Subclones were obtained by digestion with various enzymes and a subclone containing 4.9 kb from the HindIII site to KPnI was found that expressed CS6. This clone was designated M285. Expression of CS6 was verified by transferring plasmids into E. coli HB101 and detecting CS6 in heat, saline extracts. The cloned CS6 is expressed under the same conditions as CS6 from the native 61-megadalton plasmid (Table 1). CS6 was detected in western blots of heat, saline extracts of bacteria grown on CFA, L agar or MacConkey agar. CS6 was not expressed on bacteria grown at 17° C.

TABLE 1

Regulation of CS6 Expression

| Strain: | M287 | M56 | E8775 | HB101 |
|---|---|---|---|---|
| plasmid: | pM285 | native | native | none |
| Chromosome: | HB101 | HB101 | native | HB101 |
| Media | | | | |
| CFA 37° C. | + | + | + | − |
| CFA 17° C. | − | − | − | − |
| L agar | + | + | + | − |
| MacConkey | + | + | + | − |

N-terminal sequence of CS6. The protein sequence of the N-terminus of CS6 was determined from strains E8775 and from M233, the large clone derived from E8775. The 16 kDa proteins recovered from heat, saline extracts, and ammonium sulfate precipitation of M233 yielded two amino acids at each position (except cycle 12) indicating that two proteins were present. From the strength of the two signals, a probable primary sequence and a probable secondary sequence call was made for each of fifteen cycles. Quantitative analysis of the peak areas indicated that the molar ratio of the primary sequence (CS6A) to secondary sequence (CS6B) was approximately 3:1. The presence of the same two proteins was evident from strain E8775 grown on CFA agar and on L agar.

DNA sequence of CS6 operons. The sequences of DNA cloned from E8775 (in M285) were determined. They are available from Genebank accession number U04846. The DNA sequence, when compared with sequences from another strain, were found to diverge abruptly on both sides of the common area. Four open reading frames were detected. These were designated cssA, cssB, cssC, and cssD for CS six.

The GC content of the DNA is 34% and the codon usage is in the range found for Escherichia coli genes that are expressed at low or very low levels as defined by Osawa et al (*Prokaryotic Genetic Code. Experentia* 46:1097–1106 (1990)).

Genes encoding CS6 structural genes. The four open reading frames are preceded by consensus sequences for binding RNA polymerase and ribosomes. DNA and deduced amino acid sequence of cssA, a CS6 structural protein. The DNA sequence of the entire operon is available from Genebank accession number U04844. The deduced amino acid sequence from E8775 is given. The arrow indicates the site of cleavage of the signal peptide. The protein sequence is associated with the sequence for the second construct:

```
      -35                    -10                    RBS
TTGACACATTACGAATGTTATGTATACAATAAAAATGATTATAGCAATATTAATGGTGTTAT

ATGAAGAAAACAATTGGTTTAATTCTAATTCTTGCTTCATTCGGCAGCCATGCCAGAACA
 M  K  K  T  I  G  L  I  L  I  L  A  S  F  G  S  H  A  R  T          2
                                                       ↑
GAAATAGCGACTAAAAACTTCCCAGTATCAACGACTATTTCAAAAAGTTTTTTTGCACCT
 E  I  A  T  K  N  F  P  V  S  T  T  I  S  K  S  F  F  A  P         22

GAACCACGAATACAGCCTTCTTTTGGTGAAAATGTTGGAAAGGAAGGAGCTTTATTATTT
 E  P  R  I  Q  P  S  F  G  E  N  V  G  K  E  G  A  L  L  F         42

AGTGTGAACTTAACTGTTCCTGAAAATGTATCCCAGGTAACGGTCTACCCTGTTTATGAT
 S  V  N  L  T  V  P  E  N  V  S  Q  V  T  V  Y  P  V  Y  D         62

GAAGATTATGGGTTAGGACGACTAGTAAATACCGCTGATGCTTCCCAATCAATAATCTAC
 E  D  Y  G  L  G  R  L  V  N  T  A  D  A  S  Q  S  I  I  Y         82

CAGATTGTTGATGAGAAAGGGAAAAAAATGTTAAAAGATCATGGTGCAGAGGTTACACCT
 Q  I  V  D  E  K  G  K  K  M  L  K  D  H  G  A  E  V  T  P        102

AATCAACAAATAACTTTTAAAGCGCTGAATTATACTAGCGGGGAAAAAAAAATATCTCCT
 N  Q  Q  I  T  F  K  A  L  N  Y  T  S  G  E  K  K  I  S  P        122

GGAATATATAACGATCAGGTTATGGTTGGTTACTATGTAAACTAA (Seq. #4)
 G  I  Y  N  D  Q  V  M  V  G  Y  Y  V  N  *   (Seq. #5)           136
```

The first open reading frame, cssA was identified as the gene for the CS6 structural protein CS6A designated as the primary protein based on the amino acid N-terminal sequence. cssA includes a signal sequence that is typical for many exported proteins. The deduced CssA protein from E8775 has 136 residues, as shown above and in Table 2. The molecular weight agrees with that previously determined from SDS PAGE. No homologous proteins were found by searching the protein databases, but conserved residues are present near the C-terminus and this is typical of fimbrial subunits that are carried across the periplasm by chaperons.

TABLE 2

Characteristics of proteins Reduced from CS6 Operons

| Protein | Source | Number of Residues | Molecular Weight | Isoelectric Point |
|---|---|---|---|---|
| CssA (CS6A) | E8775 | 136 | 15,058 | 5.27 |
| CssB (CS6B) | E8775 | 146 | 15,877 | 4.40 |
| CssC | E8775 | 212 | 24,551 | 10.24 |
| CssD | E8775 | 802 | 90,393 | 9.97 | cssB begins 17 bases downstream from cssA. There is a typical signal sequence. cssB was identified as the gene for the CS6 structural protein CS6B designated as the secondary protein based on the amino acid N-terminal sequence. The C-terminus matches the consensus typical of fimbrial subunits. The sequence from E8775 is given. The arrow indicates the site of cleavage of the signal peptide.

```
MLKKIISAIA LIAGTSGVVN A GNWQYKSLDV NVNIEQNFIP DIDSAVRIIP    (Seq. #6)
                    ↑

VNYDSDPKLD SQLYTVEMTI PAGVSAVKIA PTDSLTSSGQ QIGKLVNVNN

PDQNMNYYIR KDSGAGNFMA GQKGSFPVKE NTSYTFSAIY TGGEYPNSGY

SSGTYAGNLT VSFYSN
```

A region of dyad symmetry is present 6 bases downstream from CssB in both clones. The sequence is GGCCGCATTATTGCGGCC(Seq. #2) in E8775 ETEC. Underlined bases form the GC rich stem.

Genes with homology to fimbrial accessory proteins. cssC begins 48 bases downstream from cssB. It has a typical signal sequence. The deduced proteins from both clones have 212 residues with 7 differences. A search of protein databases indicated CssC is homologous to chaperone proteins necessary for expression of Pap, CS3, K88, K99, CS31A, S, and Type 1 fimbriae of *E. coli* and SEF14 of *Salmonella enteritidis*, F1 and pH6 antigen of *Yersinia pestis*, Type 3 of *Klebsiella pneumoniae*, Type b of *Haemophilus influenzae*, and filamentous heamagglutinin of *Bordetella pertussis*. The structure of PapD, the chaperone protein for Pap fimbriae, has been solved by X-ray crystallography and regions important for conserving the structural domains have been identified. CssC conforms to the following consensus. Below is the deduced amino acid sequence of cssC. The * indicates conservative amino acid replacements. Dots are gaps necessary for aligning all sequences. Boxes indicate beta strands as defined for PapD. The designation of the beta strands for domain 1 (A1 through G1) and domain 2 (A2-G2) are given below each box.

```
                                                                            (Seq. #7)
     *  *R***        * *              *** ** *          ****P*****
NNF EINKTRVIYS DSTP SVQISNN KAYP.. LIIQSNVWDES NNKNH..D FIATPPIFKM
     A1           B1              C1                     D1

*    * ****       **    E ** ** *  P*                        * * *
ESES RNIIKIIK TTI..NLPDSQE SMRWLCIESM PPIEKST..KINRKEGRTDSINISI     110
     E1                    F1

*K****  P*  *       *     *   * * N  *P**   *** *
     RGCIKLIYR PASVPSPVFNN.IVEK LKWHK NGKY LVLKN NTPYY ISFSEVF      160
     G1                         A2    B2   C2

* *  P  *   *  *          *     *D G*
         FDSDKV..NNAKD ILYVK PY SEKKID ISN..RIIKKI KWAMI DDAGAKT KLYESIL
                       D2       E2              F2              G2
```

CssD begins 14 bases upstream of the end of cssC. When compared with a second sequence there are 28 differences between CssD from E8775 and the other sequence. The deduced protein from cssD is homologous to molecular ushers found in operons of Pap, CS3, K88, K99 and Type 1 fimbriae of E. coli and SEF14 of Salmonel-la enteritidis, F1 of Yersinia pestis, and Type 3 of Klebsiella pneumoniae. Overall, CssD and the other proteins are only around 30% identical and around 50% similar. Asterisks above the CssD sequences indicates amino acids conserved relative to molecular ushers.

with five distinct insertion sequences. The homologies include 3% to 32% of each insertion sequence but not entire insertion sequences. The homology of and Iso-IS1 in E8775 continues beyond the clones we have sequenced and may be a complete insertion sequences in the native plasmids.

It should be noted that minor variation in bases of the peptides does not destroy antigenicity. A protein having at least 60% homology with the CS6 A and B proteins identified herein having conservative substitution would be expected to have desirable properties.

As indicated previously, bacteria transformed with plasmids which express the CS6-A and CS6-B proteins may be

```
                 *****  *  **        *    **
MNQFYKKSHYSIQKHQITGLLFLLFIYPFSTSYGNEQFSFDSRFLPSGYN        50 (Seq. #8)

*  ** G Y *** *N       * *      * C**     *  *
YSLNSNLPPEGEYLVDIYINKIKKESAIIPFYIKGNKLVPCLSKEKISSL       100

G*  *  * *C**  **   *  **  *  **  *  **   *      *  *
GININNNDNTECVETSKAGISNISFEFSSLRLFIAVPKNLLSEIDKISSK       150

* G* *********         ** * ** * W**        *
DIDNGIHALFFNYQVNTRLANNKNRYDYISVSPNINYFSWRLRNLFEFNQ       200

****** *      * *G* ***  ***    * G* *  **
NNDEKTWERNYTYLEKSFYDKKLNLVVGESYTNSNVYNNYSFTGISVSTD       250

M       *  *  *  **A *    *  *  *      V**G*F**
TDMYTPSEIDYTPEIHGVADSDSQIIVRQGNTIIINESVPAGPFSFPITN       300

*    *  *   *  *  *    *    *  *   ****  **   *  ** *
LMYTGGQLNVEITDIYGNKKQYTVNNSSLPVMRKAGLMVYNFISGKLTKK       350

*  *    *G     *****  *  **  *  G**   *G  G*
NSEDGDFFTQGDINYGTHYNSTLFGGYQFSKNYFNLSTGIGTDLGFSGAW       400

* ** *        *     *   *    *    * ****     *   * ***
LLHVSRSNFKNKNGYNINLQQNTQLRPFNAGVNFDYAYRKKRYVELSDIG       450

** * ****  *   *  *  *        Y*
WHGNLYNQLKNSFSLSLSKSLNKYGNFSLDYNKMKYWDNAYDSNSMSIRY       500

*  ***P*         * *     **
FFKFMRAMITTNCSLNKYQSYEKKDKRFSINISLPLTKDYGHISSNYSFS       550

*    **  **   *   *  * *                    *
NANTGTATSSVGLNGSFFNDARLNWNIQQNRTTRNNGYTDNTSYIATSYA       600

*  *  *  **           * G ***    ** *     *  *  ***
SPYGVFTGSYSGSNKYSSQFYSASGGIVLHSDGVAFTQKAGDTSALVRID       650

*   *  * *     G  **    *   *  *  * **   **    *
NISDIKIGNTPGVYTGYNGFALIPHLQPFKKNTILINDKGIPDGITLANI       700

****  ****    *    *     ** *    **   ****   *
KKQVIPSRGAIVKVKFDAKKGNDILFKLTTKDGKTPPLGAIAHEKNGKQI       750

****   *  *          *  * *       C            *
NTGIVDDDGMLYMSGLSGTGIINVTWNGKVCSFPFSEKDISSKQLSVVNK       800

C
QC                                                       802
```

But comparison with the protein from another strain, the sequence data shows the proteins have areas of high homology dispersed throughout, especially the first 410 residues. CssD has 4 cysteines (residues 91, 112, and two near the C-terminus) which are conserved in all ushers.

A region of dyad symmetry is present 347 base pairs into the CssD gene in both clones. The calculated free energy value of these structures is −7.2 kcal.

DNA flanking the CS6 genes. When compared with another strain, the DNA sequences of the two clones diverge immediately downstream of cssD and 96 bases upstream of cssA. The non-homologous flanking regions have homology administered by mouth. If the transformed bacteria are attenuated strains, they may be delivered live. It is also possible to administer killed bacteria. Carbonated beverages such as carbonated water are particularly useful as carriers which are inexpensive. When the bacteria are administered in a carrier wherein the pH is not over 7, an antacid may be given with the bacteria.

The CS6 A and CS6 B proteins may also be at least partially purified and administered by mouth by means usually used in the art to deliver antigens to the intestinal tract, including in protected forms such as liposomes, microcrystals, microdroplets, as microcapsulated formulations or as enterically coated capsules.

What we claim is:

1. A composition for induction of a mucosal immune response comprising an isolated and purified protein containing the sequence

```
                                                    (SEQ ID NO.10)
GNWQYKSLDV NVNIEQNFIP DIDSAVRIIP VNYDSDPKLD

SQLYTVEMTI PAGVSAVKIA PTDSLTSSGQ QIGKLVNVNN

PDQNMNYYIR KDSGAGNFMA GQKGSFPVKE NTSYTFSAIY

TGGEYPNSGY SSGTYAGNLT VSFYSN
``` in a pharmaceutically acceptable carrier wherein the pharmaceutically acceptable carrier is selected from the group consisting of liposomes, microcrystals, microdroplets, microcapsulated formulations and enterically coated capsules.

2. A method of inducing a mucosal immune response comprising the step of: administering the composition of claim 1 to a subject.

* * * * *

SEQUENCE LISTING (1) GENERAL INFORMATION:

(iii) NUMBER OF SEQUENCES: 10

(2) INFORMATION FOR SEQ ID NO: 1:

(i) SEQUENCE CHARACTERISTICS:
       (A) LENGTH: 4875 base pairs
       (B) TYPE: nucleic acid
       (C) STRANDEDNESS: single
       (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 1:

```
AAGCTTGTAA CCAGTTGATA AAAATATATC ACGCTGGGAA TGACGTGATG TATATACGGA      60

GCAGCTATGT CGGAACAGAT ATTTTCCTAT CGGTATGCGT TGTGAGTAAG CGTAAAGCCA     120

ATGCTGTCTG TAACTCCTGA TCCTTGCAGA CTAAATTAGA GCTCCTTCTA AATTAGACGG     180

ATGGATAAAC CTACAGACTG GCGCTCTGGG TCTCGCCGGA TATTTTCTAA TGAATTTAAG     240

CTTCATATGG TTGAACTGGC TTCGAAACCA AATGCCAATG TCGCACAACT GGCTCGGGAA     300

CATGGCGTTG ATAACAACCT GATTTTTAAA TAGCTACGCC TCTGGCAAAG AGAAGGACGT     360

ATTTCTCGTA GAATGCCTCC AACTATTGTA GGCCCTACAG TACCACTGAG GTAGCCTGAA     420

TTTAAAGCCG AAGCGGTCAG AACTGTTCTT GGTGTGAACG TAGCACTCAC CAATAAAAGC     480

ATCAATACGG TGCTCTGTTG ACACATTACG AATGTTATGT ATACAATAAA AATGATTATA     540

GCAATATTAA TGGTGTTATA TGAAGAAAAC AATTGGTTTA ATTCTAATTC TTGCTTCATT     600

CGGCAGCCAT GCCAGAACAG AAATAGCGAC TAAAAACTTC CCAGTATCAA CGACTATTTC     660

AAAAAGTTTT TTTGCACCTG AACCACGAAT ACAGCCTTCT TTTGGTGAAA ATGTTGGAAA     720

GGAAGGAGCT TTATTATTTA GTGTGAACTT AACTGTTCCT GAAAATGTAT CCCAGGTAAC     780

GGTCTACCCT GTTTATGATG AAGATTATGG GTTAGGACGA CTAGTAAATA CCGCTGATGC     840

TTCCCAATCA ATAATCTACC AGATTGTTGA TGAGAAAGGG AAAAAAATGT TAAAAGATCA     900

TGGTGCAGAG GTTACACCTA ATCAACAAAT AACTTTTAAA GCGCTGAATT ATACTAGCGG     960

GGAAAAAAAA ATATCTCCTG GAATATATAA CGATCAGGTT ATGGTTGGTT ACTATGTAAA    1020

CTAAATACTG GAAGTATGAT TATGTTGAAA AAAATTATTT CGGCTATTGC ATTAATTGCA    1080

GGAACTTCCG GAGTGGTAAA TGCAGGAAAC TGGCAATATA AATCTCTGGA TGTAAATGTA    1140

AATATTGAGC AAAATTTTAT TCCAGATATT GATTCCGCTG TTCGTATAAT ACCTGTTAAT    1200

TACGATTCGG ACCCGAAACT GGATTCACAG TTATATACGG TTGAGATGAC GATCCCTGCA    1260

GGTGTAAGCG CAGTTAAAAT CGCACCAACA GATAGTCTGA CATCTTCTGG ACAGCAGATC    1320

GGAAAGCTGG TTAATGTAAA CAATCCAGAT CAAAATATGA ATTATTATAT CAGAAAGGAT    1380

TCTGGCGCTG GTAACTTTAT GGCAGGACAA AAAGGATCCT TTCCTGTCAA AGAGAATACG    1440

TCATACACAT TCTCAGCAAT TTATACTGGT GGCGAATACC CTAATAGCGG ATATTCGTCT    1500

GGTACTTATG CAGGAAATTT GACTGTATCA TTTTACAGCA ATTAAAAAAA GGCCGCATTA    1560

TTGCGGCCAT TGACGATACT GCTAGGCAAA AATATGAAAT CAAAGTTAAT TATACTATTG    1620

ACGTTAGTGC CATTTTCATC TTTTTCAACA GGAAATAATT TTGAAATAAA TAAGCACGA    1680
```

-continued

```
GTAATTTACT CTGACAGCAC ACCATCAGTT CAAATATCAA ATAATAAAGC ATATCCTTTA    1740

ATTATTCAAA GCAATGTATG GGATGAAAGC AATAATAAAA ATCATGACTT TATAGCAACA    1800

CCACCGATTT TTAAAATGGA AAGTGAAAGT CGGAATATAA TAAAAATAAT TAAAACAACT    1860

ATTAATTTGC CGGACTCTCA GGAAAGTATG AGATGGTTAT GTATTGAATC AATGCCACCA    1920

ATAGAAAAAA GTACTAAAAT AAACAGAAAA GAAGGAAGGA CAGACAGTAT TAATATCAGC    1980

ATTCGGGGGT GCATTAAACT GATATATCGA CCTGCCAGTG TTCCGTCTCC TGTTTTTAAT    2040

AATATAGTAG AAAAATTAAA ATGGCATAAA AATGGAAAGT ATCTTGTATT AAAAAATAAT    2100

ACACCCTATT ACATTAGCTT TTCTGAGGTT TTTTTTGATT CAGATAAAGT AAACAATGCA    2160

AAAGATATTT TATATGTAAA ACCATACTCA GAGAAGAAAA TAGATATCAG CAACAGAATA    2220

ATAAAAAAAA TCAAATGGGC TATGATTGAT GATGCTGGCG CAAAAACAAA ACTTTATGAA    2280

TCAATTTTAT AAAAAATCTC ATTACAGTAT ACAAAAACAT CAGATTACAG GCTTGCTTTT    2340

TTTGCTATTT ATATATCCTT TCTCAACCTC ATATGGAAAT GAACAATTTA GTTTTGACTC    2400

ACGATTCCTA CCATCAGGTT ATAATTACTC TTTAAATAGT AACTTACCTC CTGAAGGTGA    2460

GTATCTGGTT GATATTTATA TTAACAAAAT AAAAAAGGAG TCCGCGATTA TTCCTTTTTA    2520

TATAAAGGA AATAAACTTG TACCATGTTT ATCAAAAGAA AAAATTTCAT CTTTGGGTAT    2580

CAACATTAAT AATAACGACA ACACAGAGTG TGTAGAAACA AGTAAGGCAG GTATTAGTAA    2640

TATCAGCTTT GAGTTTAGCT CTCTTCGTTT GTTTATTGCT GTACCGAAAA ATCTTCTGTC    2700

TGAGATTGAT AAAATATCAT CAAAGGATAT AGATAACGGG ATTCATGCTT TATTTTTTAA    2760

TTATCAAGTA AATACAAGGC TAGCCAATAA TAAAAATCGT TATGATTACA TTTCTGTTTC    2820

ACCAAATATA AATTATTTTT CATGGCGGTT GCGTAATCTT TTTGAATTTA ACCAAAACAA    2880

CGATGAAAAA ACATGGGAAA GAAACTACAC TTATCTAGAA AAAAGTTTTT ATGATAAAAA    2940

GCTAAACTTA GTCGTTGGTG AAAGTTATAC GAATTCAAAT GTTTATAATA ACTACTCTTT    3000

TACTGGTATT TCAGTTTCTA CAGATACAGA TATGTATACG CCAAGTGAAA TCGATTATAC    3060

ACCAGAAATT CATGGAGTGG CTGATTCAGA CTCTCAGATT ATTGTCAGGC AAGGCAACAC    3120

CATTATCATT AATGAAAGTG TTCCAGCCGG ACCGTTCTCA TTTCCAATAA CCAATCTCAT    3180

GTATACTGGG GGGCAACTTA ATGTGGAGAT AACAGATATT TATGGAAATA AAAAACAATA    3240

TACTGTCAAT AATTCCTCTC TTCCTGTTAT GAGAAAAGCG GGACTAATGG TATATAATTT    3300

TATATCTGGG AAATTAACAA AAAAAAATAG TGAGGATGGT GATTTTTTTA CTCAAGGTGA    3360

TATTAACTAC GGTACTCACT ATAACAGCAC ACTATTCGGT GGATATCAGT TTAGTAAAAA    3420

TTATTTTAAC TTATCTACTG GTATAGGCAC TGATCTGGGA TTTTCTGGAG CATGGCTACT    3480

ACACGTTAGC AGAAGTAATT TTAAGAATAA AAATGGATAT AATATTAATC TACAACAAAA    3540

CACTCAGTTA AGACCATTCA ATGCCGGGGT TAATTTCGAT TACGCATACA GAAAAAAAAG    3600

GTATGTGGAA CTTTCCGACA TTGGCTGGCA TGGTAATTTA TATAATCAAC TTAAAAATAG    3660

TTTTTCTTTA TCCTTGTCAA AATCATTGAA TAAATACGGA AATTTCTCAC TTGATTATAA    3720

CAAAATGAAA TACTGGGATA ATGCGTATGA TAGTAACTCA ATGTCGATTC GTTATTTTTT    3780

TAAATTCATG CGAGCAATGA TTACAACAAA TTGTTCTTTA AATAAATATC AATCTTATGA    3840

AAAAAAAGAT AAAAGATTTA GTATTAATAT ATCATTGCCT TTAACCAAAG ATTACGGGCA    3900

CATATCTTCA AACTATTCAT TTTCCAATGC AAATACAGGA ACGGCAACCA GTTCTGTAGG    3960

CTTAAACGGT AGTTTTTTTA ATGACGCAAG ATTAAACTGG AACATTCAGC AGAACAGAAC    4020
```

```
GACCCGTAAC AATGGATATA CTGATAATAC CAGTTACATA GCAACCAGCT ATGCCTCTCC    4080

CTATGGCGTT TTTACTGGTT CATATTCAGG ATCGAACAAG TATTCAAGCC AGTTTTATTC    4140

TGCATCGGGA GGTATTGTTT TGCATAGCGA TGGCGTAGCT TTTACTCAAA AAGCCGGAGA    4200

TACCTCTGCT CTTGTCCGTA TTGATAATAT TTCTGATATA AAAATTGGTA ACACTCCTGG    4260

TGTTTATACT GGGTATAATG GTTTTGCTTT AATTCCTCAT CTTCAGCCGT TCAAAAAAAA    4320

CACCATTTTA ATTAATGATA AAGGAATTCC AGACGGTATT ACTCTTGCTA ATATAAAAAA    4380

ACAAGTTATC CCATCACGAG GAGCTATTGT TAAAGTAAAA TTTGATGCTA AAAAAGGCAA    4440

TGACATTTTG TTTAAGCTTA CAACTAAAGA TGGAAAAACG CCCCCATTAG GAGCTATAGC    4500

CCATGAAAAA AATGGAAAAC AGATTAATAC GGGTATCGTT GACGATGATG GTATGCTTTA    4560

TATGTCTGGA TTATCAGGGA CAGGGATTAT TAATGTAACA TGGAATGGAA AAGTCTGTTC    4620

ATTTCCTTTT TCAGAAAAAG ATATATCTAG CAAACAATTA TCTGTTGTAA ATAAACAATG    4680

TTAGGTAGTG CATCCAATTA GTAGAACATG TGTTTTTCGA TAAACGCTCC GATCTCTTTT    4740

TCGTGGATCT CAACTGAGCG TGAGAAGCAG ATTGTTTTAC GAGCCAACCG CTTAATGCGG    4800

GTGCGTAGCG TCAGATTATT ACGCTCAATG CGTTGGGTGA ATATTTTGCC GGTCAGATGC    4860

TTATTCTTCG GTACC                                                    4875

(2) INFORMATION FOR SEQ ID NO: 2:

(i) SEQUENCE CHARACTERISTICS:
        (A) LENGTH: 18 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 2:

GGCCGCATTA TTGCGGCC                                                       18

(2) INFORMATION FOR SEQ ID NO: 3:

(i) SEQUENCE CHARACTERISTICS:
        (A) LENGTH: 22 base pairs
        (B) TYPE: nucleic acid
        (C) STRANDEDNESS: single
        (D) TOPOLOGY: unknown (ii) MOLECULE TYPE: DNA (genomic)

(iii) HYPOTHETICAL: NO (iv) ANTI-SENSE: NO (xi) SEQUENCE DESCRIPTION: SEQ ID NO: 3:

GGCCGCATTA TTGATTGCGG CC                                                  22

(2) INFORMATION FOR SEQ ID NO: 4:

(i) SEQUENCE CHARACTERISTICS:
        (A) LENGTH: 527 base pairs
        (B) TYPE: nucleic acid
        (C) STRANDEDNESS: single
        (D) TOPOLOGY: unknown (ii) MOLECULE TYPE: DNA (genomic)
```

-continued (iii) HYPOTHETICAL: NO (iv) ANTI-SENSE: NO (xi) SEQUENCE DESCRIPTION: SEQ ID NO: 4:

```
TTGACACATT ACGAATGTTA TGTATACAAT AAAAATGATT ATAGCAATAT TAATGGTGTT      60
ATATGAAGAA AACAATTGGT TTAATTCTAA TTCTTGCTTC ATTCGGCAGC CATGCCAGAA     120
CAGAAATAGC GACTAAAAAC TTCCCAGTAT CAACGACTAT TTCAAAAAGT TTTTTTGCAC     180
CTGAACCACG AATACAGCCT TCTTTTGGTG AAAATGTTGG AAAGGAAGGA GCTTTATTAT     240
TTAGTGTGAA CTTAACTGTT CCTGAAAATG TATCCCAGGT AACGGTCTAC CCTGTTTATG     300
ATGAAGATTA TGGGTTAGGA CGACTAGTAA ATACCGCTGA TGCTTCCCAA TCAATAATCT     360
ACCAGATTGT TGATGAGAAA GGGAAAAAAA TGTTAAAAGA TCATGGTGCA GAGGTTACAC     420
CTAATCAACA AATAACTTTT AAAGCGCTGA ATTATACTAG CGGGGAAAAA AAAATATCTC     480
CTGGAATATA TAACGATCAG GTTATGGTTG GTTACTATGT AAACTAA                  527
```

(2) INFORMATION FOR SEQ ID NO: 5:

(i) SEQUENCE CHARACTERISTICS:
        (A) LENGTH: 154 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 5:

```
Met Lys Lys Thr Ile Gly Leu Ile Leu Ile Leu Ala Ser Phe Gly Ser
1               5                   10                  15

His Ala Arg Thr Glu Ile Ala Thr Lys Asn Phe Pro Val Ser Thr Thr
            20                  25                  30

Ile Ser Lys Ser Phe Phe Ala Pro Glu Pro Arg Ile Gln Pro Ser Phe
        35                  40                  45

Gly Glu Asn Val Gly Lys Glu Gly Ala Leu Leu Phe Ser Val Asn Leu
    50                  55                  60

Thr Val Pro Glu Asn Val Ser Gln Val Thr Val Tyr Pro Val Tyr Asp
65                  70                  75                  80

Glu Asp Tyr Gly Leu Gly Arg Leu Val Asn Thr Ala Asp Ala Ser Gln
                85                  90                  95

Ser Ile Ile Tyr Gln Ile Val Asp Glu Lys Gly Lys Lys Met Leu Lys
            100                 105                 110

Asp His Gly Ala Glu Val Thr Pro Asn Gln Gln Ile Thr Phe Lys Ala
        115                 120                 125

Leu Asn Tyr Thr Ser Gly Glu Lys Lys Ile Ser Pro Gly Ile Tyr Asn
    130                 135                 140

Asp Gln Val Met Val Gly Tyr Tyr Val Asn
145                 150
```

(2) INFORMATION FOR SEQ ID NO: 6:

(i) SEQUENCE CHARACTERISTICS:
        (A) LENGTH: 167 amino acids
        (B) TYPE: amino acid
        (C) STRANDEDNESS: single
        (D) TOPOLOGY: unknown

```
            (ii) MOLECULE TYPE: peptide (iii) HYPOTHETICAL: NO (iv) ANTI-SENSE: NO (xi) SEQUENCE DESCRIPTION: SEQ ID NO: 6:

Met Leu Lys Lys Ile Ile Ser Ala Ile Ala Leu Ile Ala Gly Thr Ser
1               5                   10                  15

Gly Val Val Asn Ala Gly Asn Trp Gln Tyr Lys Ser Leu Asp Val Asn
                20                  25                  30

Val Asn Ile Glu Gln Asn Phe Ile Pro Asp Ile Asp Ser Ala Val Arg
            35                  40                  45

Ile Ile Pro Val Asn Tyr Asp Ser Asp Pro Lys Leu Asp Ser Gln Leu
        50                  55                  60

Tyr Thr Val Glu Met Thr Ile Pro Ala Gly Val Ser Ala Val Lys Ile
65                  70                  75                  80

Ala Pro Thr Asp Ser Leu Thr Ser Ser Gly Gln Gln Ile Gly Lys Leu
                85                  90                  95

Val Asn Val Asn Asn Pro Asp Gln Asn Met Asn Tyr Tyr Ile Arg Lys
                100                 105                 110

Asp Ser Gly Ala Gly Asn Phe Met Ala Gly Gln Lys Gly Ser Phe Pro
            115                 120                 125

Val Lys Glu Asn Thr Ser Tyr Thr Phe Ser Ala Ile Tyr Thr Gly Gly
        130                 135                 140

Glu Tyr Pro Asn Ser Gly Tyr Ser Ser Gly Thr Tyr Ala Gly Asn Leu
145                 150                 155                 160

Thr Val Ser Phe Tyr Ser Asn
                165

(2) INFORMATION FOR SEQ ID NO: 7:

(i) SEQUENCE CHARACTERISTICS:
           (A) LENGTH: 212 amino acids
           (B) TYPE: amino acid
           (C) STRANDEDNESS: single
           (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 7:

Asn Asn Phe Glu Ile Asn Lys Thr Arg Val Ile Tyr Ser Asp Ser Thr
1               5                   10                  15

Pro Ser Val Gln Ile Ser Asn Asn Lys Ala Tyr Pro Leu Ile Ile Gln
                20                  25                  30

Ser Asn Val Trp Asp Glu Ser Asn Lys Asn His Asp Phe Ile Ala
            35                  40                  45

Thr Pro Pro Ile Phe Lys Met Glu Ser Glu Ser Arg Asn Ile Ile Lys
        50                  55                  60

Ile Ile Lys Thr Thr Ile Asn Leu Pro Asp Ser Gln Glu Ser Met Arg
65                  70                  75                  80

Trp Leu Cys Ile Glu Ser Met Pro Pro Ile Glu Lys Ser Thr Lys Ile
                85                  90                  95

Asn Arg Lys Glu Gly Arg Thr Ser Ile Asn Ile Ser Ile Arg Gly
                100                 105                 110
```

```
Cys Ile Lys Leu Ile Tyr Arg Pro Ala Ser Val Pro Ser Pro Val Phe
        115                 120                 125

Asn Asn Ile Val Glu Lys Leu Lys Trp His Lys Asn Gly Lys Tyr Leu
    130                 135                 140

Val Leu Lys Asn Asn Thr Pro Tyr Tyr Ile Ser Phe Ser Glu Val Phe
145                 150                 155                 160

Phe Asp Ser Asp Lys Val Asn Asn Ala Lys Asp Ile Leu Tyr Val Lys
                165                 170                 175

Pro Tyr Ser Glu Lys Lys Ile Asp Ile Ser Asn Arg Ile Ile Lys Lys
            180                 185                 190

Ile Lys Trp Ala Met Ile Asp Asp Ala Gly Ala Lys Thr Lys Leu Tyr
        195                 200                 205

Glu Ser Ile Leu
    210

(2) INFORMATION FOR SEQ ID NO: 8:

(i) SEQUENCE CHARACTERISTICS:
        (A) LENGTH: 802 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 8:

Met Asn Gln Phe Tyr Lys Lys Ser His Tyr Ser Ile Gln Lys His Gln
1               5                   10                  15

Ile Thr Gly Leu Leu Phe Leu Leu Phe Ile Tyr Pro Phe Ser Thr Ser
            20                  25                  30

Tyr Gly Asn Glu Gln Phe Ser Phe Asp Ser Arg Phe Leu Pro Ser Gly
        35                  40                  45

Tyr Asn Tyr Ser Leu Asn Ser Asn Leu Pro Pro Glu Gly Glu Tyr Leu
50                  55                  60

Val Asp Ile Tyr Ile Asn Lys Ile Lys Lys Glu Ser Ala Ile Ile Pro
65                  70                  75                  80

Phe Tyr Ile Lys Gly Asn Lys Leu Val Pro Cys Leu Ser Lys Glu Lys
                85                  90                  95

Ile Ser Ser Leu Gly Ile Asn Ile Asn Asn Asp Asn Thr Glu Cys
            100                 105                 110

Val Glu Thr Ser Lys Ala Gly Ile Ser Asn Ile Ser Phe Glu Phe Ser
        115                 120                 125

Ser Leu Arg Leu Phe Ile Ala Val Pro Lys Asn Leu Leu Ser Glu Ile
    130                 135                 140

Asp Lys Ile Ser Ser Lys Asp Ile Asp Asn Gly Ile His Ala Leu Phe
145                 150                 155                 160

Phe Asn Tyr Gln Val Asn Thr Arg Leu Ala Asn Asn Lys Asn Arg Tyr
                165                 170                 175

Asp Tyr Ile Ser Val Ser Pro Asn Ile Asn Tyr Phe Ser Trp Arg Leu
            180                 185                 190

Arg Asn Leu Phe Glu Phe Asn Gln Asn Asn Asp Glu Lys Thr Trp Glu
        195                 200                 205

Arg Asn Tyr Thr Tyr Leu Glu Lys Ser Phe Tyr Asp Lys Lys Leu Asn
```

-continued

```
                210                 215                 220
Leu Val Val Gly Glu Ser Tyr Thr Asn Ser Asn Val Tyr Asn Asn Tyr
225                 230                 235                 240

Ser Phe Thr Gly Ile Ser Val Ser Thr Asp Thr Asp Met Tyr Thr Pro
                245                 250                 255

Ser Glu Ile Asp Tyr Thr Pro Glu Ile His Gly Val Ala Asp Ser Asp
                260                 265                 270

Ser Gln Ile Ile Val Arg Gln Gly Asn Thr Ile Ile Ile Asn Glu Ser
                275                 280                 285

Val Pro Ala Gly Pro Phe Ser Phe Pro Ile Thr Asn Leu Met Tyr Thr
290                 295                 300

Gly Gly Gln Leu Asn Val Glu Ile Thr Asp Ile Tyr Gly Asn Lys Lys
305                 310                 315                 320

Gln Tyr Thr Val Asn Asn Ser Ser Leu Pro Val Met Arg Lys Ala Gly
                325                 330                 335

Leu Met Val Tyr Asn Phe Ile Ser Gly Lys Leu Thr Lys Lys Asn Ser
                340                 345                 350

Glu Asp Gly Asp Phe Phe Thr Gln Gly Asp Ile Asn Tyr Gly Thr His
                355                 360                 365

Tyr Asn Ser Thr Leu Phe Gly Gly Tyr Gln Phe Ser Lys Asn Tyr Phe
370                 375                 380

Asn Leu Ser Thr Gly Ile Gly Thr Asp Leu Gly Phe Ser Gly Ala Trp
385                 390                 395                 400

Leu Leu His Val Ser Arg Ser Asn Phe Lys Asn Lys Asn Gly Tyr Asn
                405                 410                 415

Ile Asn Leu Gln Gln Asn Thr Gln Leu Arg Pro Phe Asn Ala Gly Val
                420                 425                 430

Asn Phe Asp Tyr Ala Tyr Arg Lys Lys Arg Tyr Val Glu Leu Ser Asp
                435                 440                 445

Ile Gly Trp His Gly Asn Leu Tyr Asn Gln Leu Lys Asn Ser Phe Ser
                450                 455                 460

Leu Ser Leu Ser Lys Ser Leu Asn Lys Tyr Gly Asn Phe Ser Leu Asp
465                 470                 475                 480

Tyr Asn Lys Met Lys Tyr Trp Asp Asn Ala Tyr Asp Ser Asn Ser Met
                485                 490                 495

Ser Ile Arg Tyr Phe Phe Lys Phe Met Arg Ala Met Ile Thr Thr Asn
                500                 505                 510

Cys Ser Leu Asn Lys Tyr Gln Ser Tyr Glu Lys Lys Asp Lys Arg Phe
                515                 520                 525

Ser Ile Asn Ile Ser Leu Pro Leu Thr Lys Asp Tyr Gly His Ile Ser
                530                 535                 540

Ser Asn Tyr Ser Phe Ser Asn Ala Asn Thr Gly Thr Ala Thr Ser Ser
545                 550                 555                 560

Val Gly Leu Asn Gly Ser Phe Phe Asn Asp Ala Arg Leu Asn Trp Asn
                565                 570                 575

Ile Gln Gln Asn Arg Thr Thr Arg Asn Asn Gly Tyr Thr Asp Asn Thr
                580                 585                 590

Ser Tyr Ile Ala Thr Ser Tyr Ala Ser Pro Tyr Gly Val Phe Thr Gly
                595                 600                 605

Ser Tyr Ser Gly Ser Asn Lys Tyr Ser Ser Gln Phe Tyr Ser Ala Ser
                610                 615                 620

Gly Gly Ile Val Leu His Ser Asp Gly Val Ala Phe Thr Gln Lys Ala
625                 630                 635                 640
```

-continued

```
Gly Asp Thr Ser Ala Leu Val Arg Ile Asp Asn Ile Ser Asp Ile Lys
            645                 650                 655

Ile Gly Asn Thr Pro Gly Val Tyr Thr Gly Tyr Asn Gly Phe Ala Leu
            660                 665                 670

Ile Pro His Leu Gln Pro Phe Lys Lys Asn Thr Ile Leu Ile Asn Asp
            675                 680                 685

Lys Gly Ile Pro Asp Gly Ile Thr Leu Ala Asn Ile Lys Lys Gln Val
            690                 695                 700

Ile Pro Ser Arg Gly Ala Ile Val Lys Val Lys Phe Asp Ala Lys Lys
705                 710                 715                 720

Gly Asn Asp Ile Leu Phe Lys Leu Thr Thr Lys Asp Gly Lys Thr Pro
            725                 730                 735

Pro Leu Gly Ala Ile Ala His Glu Lys Asn Gly Lys Gln Ile Asn Thr
            740                 745                 750

Gly Ile Val Asp Asp Asp Gly Met Leu Tyr Met Ser Gly Leu Ser Gly
            755                 760                 765

Thr Gly Ile Ile Asn Val Thr Trp Asn Gly Lys Val Cys Ser Phe Pro
770                 775                 780

Phe Ser Glu Lys Asp Ile Ser Ser Lys Gln Leu Ser Val Val Asn Lys
785                 790                 795                 800

Gln Cys
```

(2) INFORMATION FOR SEQ ID NO: 9:

(i) SEQUENCE CHARACTERISTICS:
        (A) LENGTH: 136 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 9:

```
Arg Thr Glu Ile Ala Thr Lys Asn Phe Pro Val Ser Thr Thr Ile Ser
1               5                   10                  15

Lys Ser Phe Phe Ala Pro Glu Pro Arg Ile Gln Pro Ser Phe Gly Glu
            20                  25                  30

Asn Val Gly Lys Glu Gly Ala Leu Leu Phe Ser Val Asn Leu Thr Val
            35                  40                  45

Pro Glu Asn Val Ser Gln Val Thr Val Tyr Pro Val Tyr Asp Glu Asp
            50                  55                  60

Tyr Gly Leu Gly Arg Leu Val Asn Thr Ala Asp Ala Ser Gln Ser Ile
65                  70                  75                  80

Ile Tyr Gln Ile Val Asp Glu Lys Gly Lys Met Leu Lys Asp His
                    85                  90                  95

Gly Ala Glu Val Thr Pro Asn Gln Gln Ile Thr Phe Lys Ala Leu Asn
            100                 105                 110

Tyr Thr Ser Gly Glu Lys Lys Ile Ser Pro Gly Ile Tyr Asn Asp Gln
            115                 120                 125

Val Met Val Gly Tyr Tyr Val Asn
            130                 135
```

(2) INFORMATION FOR SEQ ID NO: 10:

```
    (i) SEQUENCE CHARACTERISTICS:
        (A) LENGTH: 146 amino acids
        (B) TYPE: amino acid
        (C) STRANDEDNESS: single
        (D) TOPOLOGY: unknown (ii) MOLECULE TYPE: peptide (iii) HYPOTHETICAL: NO (iv) ANTI-SENSE: NO (xi) SEQUENCE DESCRIPTION: SEQ ID NO: 10:

Gly Asn Trp Gln Tyr Lys Ser Leu Asp Val Asn Val Asn Ile Glu Gln
1               5                  10                  15

Asn Phe Ile Pro Asp Ile Asp Ser Ala Val Arg Ile Ile Pro Val Asn
            20                  25                  30

Tyr Asp Ser Asp Pro Lys Leu Asp Ser Gln Leu Tyr Thr Val Glu Met
        35                  40                  45

Thr Ile Pro Ala Gly Val Ser Ala Val Lys Ile Ala Pro Thr Asp Ser
    50                  55                  60

Leu Thr Ser Ser Gly Gln Gln Ile Gly Lys Leu Val Asn Val Asn Asn
65                  70                  75                  80

Pro Asp Gln Asn Met Asn Tyr Tyr Ile Arg Lys Asp Ser Gly Ala Gly
                85                  90                  95

Asn Phe Met Ala Gly Gln Lys Gly Ser Phe Pro Val Lys Glu Asn Thr
            100                 105                 110

Ser Tyr Thr Phe Ser Ala Ile Tyr Thr Gly Gly Glu Tyr Pro Asn Ser
        115                 120                 125

Gly Tyr Ser Ser Gly Thr Tyr Ala Gly Asn Leu Thr Val Ser Phe Tyr
    130                 135                 140

Ser Asn
145
```